United States Patent [19]

Hung et al.

[11] Patent Number: 5,098,445
[45] Date of Patent: Mar. 24, 1992

[54] ULTRAVIOLET RADIATION ABSORBING AGENT FOR BONDING TO AN OCULAR LENS

[75] Inventors: William M. Hung; Kai C. Su, both of Alpharetta, Ga.

[73] Assignee: Ciba-Geigy Corporation, Ardsley, N.Y.

[21] Appl. No.: 468,386

[22] Filed: Jan. 22, 1990

Related U.S. Application Data

[63] Continuation-in-part of Ser. No. 323,354, Mar. 14, 1989, Pat. No. 4,929,250, and a continuation-in-part of Ser. No. 323,327, Mar. 14, 1989, Pat. No. 4,936,160.

[51] Int. Cl.$^5$ .................................. D06P 5/00
[52] U.S. Cl. ............................. 8/507; 8/549; 8/648; 351/162; 544/180
[58] Field of Search ................................. 8/507

[56] References Cited

U.S. PATENT DOCUMENTS

| | | | |
|---|---|---|---|
| 4,390,676 | 6/1983 | Loshaek | 526/313 |
| 4,447,474 | 5/1984 | Neefe | 8/507 |
| 4,559,059 | 12/1985 | Su | 8/507 |
| 4,702,574 | 10/1987 | Bawa | 351/162 |
| 4,845,180 | 7/1989 | Henry et al. | 528/73 |
| 4,929,250 | 5/1990 | Hung et al. | 8/507 |
| 4,954,132 | 9/1990 | Hung et al. | 8/507 |
| 4,963,160 | 10/1990 | Hung et al. | 8/507 |

FOREIGN PATENT DOCUMENTS 885986  1/1962  United Kingdom .

*Primary Examiner*—A. Lionel Clingman
*Attorney, Agent, or Firm*—Irving Fishman; William Hervey

[57] ABSTRACT

An ultraviolet radiation absorbing contact lens and method of making the same, comprising a copolymeric hydrogel material to which is covalently bonded at least one halotriazine reactive ultraviolet radiation absorbing agent of the formula:

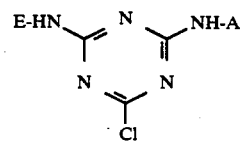

or

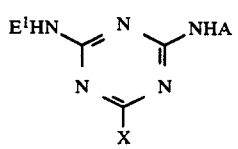

where
X = Cl or F;
E, A = an ultraviolet radiation absorbing component; and
$E^1$ = an aqueous soluble moiety.

8 Claims, No Drawings

ULTRAVIOLET RADIATION ABSORBING AGENT FOR BONDING TO AN OCULAR LENS

BACKGROUND OF THE INVENTION

The present invention relates to ultraviolet radiation absorbing contact lenses and to a method for their preparation. More particularly, the invention relates to hydrophilic or "soft" contact lenses having a reactive ultraviolet radiation absorbing agent covalently bonded to polymeric material.

Ultraviolet radiation is ever present in our environment, and consists of wave lengths between 200-400 nm. Exposure to ultraviolet radiation has been found to be the cause of several ocular pathologies. The damaging effect of ultraviolet radiation on the corneal epithelium has been known for a long time. For instance, studies have demonstrated the damaging effect of 290 nm radiation on the rabbit corneal epithelium (Cullen, A. P. (1980): *Ultraviolet Induced Lysosome Activity in Corneal Epithelium*, Graefes Arch Clin Exp. Ophthalmol 214:107-118), as well as changes in the stroma and endothelium of primary corneal layers (epithelium, stroma and endothelium) subsequent to exposure to a commercially available UV suntan lamp which emits radiation across the full spectrum from 280 nm (Ringvold, A., et al. (1985): *Changes in the Rabbit Corneal Stroma Caused by UV-Radiation*, Acta Ophthalmol. (Copenh) 63:601-606). Compounding the damage is the fact that ultraviolet radiation damage to the eye is known to be cumulative and obeys the law of reciprocity. These findings reinforce the importance of adequate ocular protection against ultraviolet radiation. Such protection is particularly recommended for people who are prone to UV exposure, patients who have had cataract surgery and patients on photo-sensitizing drugs.

Recently, contact lenses have been developed which serve to absorb ultraviolet radiation. For example, U.S. Pat. No. 4,390,676 discloses an ultraviolet absorbing contact lens formed by copolymerizing a monomer suitable for making lenses and an ultraviolet absorber for absorbing radiation having wavelengths of 340 to 450 nm. The UV absorbing compound, 2-hydroxy-4-methacryloxy-benzophenone or mixtures thereof, is incorporated into the lens' polymeric material at the molecular level. Also, U.S. Pat. No. 4,528,311 discloses ultraviolet light absorbing contact lenses made of a polymeric composition comprising copolymers of 2-hydroxy-5-acrylyloxyphenyl-2H-benzotriazole with one or more other monomers copolymerizable therewith.

The above compounds have been found to copolymerize and give protection to the material. However, the copolymerization efficiency of the compounds has proved to be inadequate. Typically, no more than 15% of the alkenyloxy-benzophenones actually become part of the polymeric chain. The remainder of the material is easily leached out by solvent extraction. Furthermore, while the hydroxy benzophenones copolymerizable with acrylate monomers are effective UV absorbers and form chemically stable copolymers, relatively large amounts, i.e. 3 to 10% by weight, must be incorporated in the polymer to obtain 85% UV absorption at 400 nm and 1 mm thickness. Also, the compounds exhibit very broad absorption bands which extend into the visible spectrum, and lenses incorporating these ingredients tend to be unacceptably yellow in color.

The above described UV absorbing lenses also possess several limitations. For instance, the absorbing agents and the lens material have different properties, and only one absorbing agent is used and appears symmetrically as a thick film on the lens. As a result, the lenses have structural weaknesses and exhibit inconsistent expansion, which in turn results in overly curved or otherwise misshapened lenses. Furthermore, the application of the agent to the lens takes a relatively long time, must be done at high temperature, and requires a high concentration of the expensive agent. Also, the use of a single absorbing agent limits the range of UV wavelengths which the lens may absorb.

There exists, therefore, a need for improved ultraviolet radiation absorbing contact lenses, as well as a method for their production.

There also exists a need for such lenses which have structural integrity, which can be prepared in relatively short time and at relatively low temperatures and which use small amounts of UV absorbing agents.

There exists a further need for such lenses which absorb a broad range of UV wavelengths.

There exists a more particular need for a lens which incorporates a relatively small amount of absorbing agent, which exhibits relatively little yellowing, and from which the absorbing agent does not leach out.

SUMMARY OF THE INVENTION

The present invention relates to ultraviolet radiation absorbing lenses, and a method for their production, comprising a UV absorbing agent covalently bonded to a polymeric lens material. The lens exhibits very little yellowing, and can be produced using a relatively small amount of the absorbing agent. Also, because of the covalent bonding, the absorbing agent does not leach from the lens.

The absorbing agent has the formula:

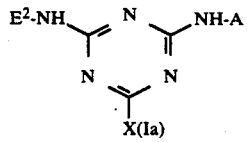

where
- X = Cl when E is a UV-absorber or Cl or F when E is not a UV-absorber;
- A = an ultraviolet radiation absorbing component; and
- $E^2$ = an aqueous soluble moiety or an ultraviolet radiation absorbing component.

The agent should be water soluble (at least in the tinting conditions of use) because the step of incorporating the agent onto the lens material is performed in an aqueous medium.

The UV absorbing components A and $E^2$ may be similar or different. If A and $E^2$ absorb radiation of different wavelengths, a lens having the agent with both components will be capable of absorbing radiation having wavelengths of the union of A and $E^2$. Also, regardless of whether the A and $E^2$ components are similar or different, less agent will be needed on the lens when both A and E are ultraviolet absorbing component.

It has also been found that the absorbing agent of the present invention can be applied to a lens at about room temperature and in a relatively short time by simply dipping or otherwise placing the lens into an aqueous medium having the agent dissolved therein. This enables the agent to be applied to the lens by an optometrist at the point of purchase, rather than at the facility where the lens is made. Therefore, the optometrist does not need to maintain a large inventory of already absorbent lenses.

DETAILED DESCRIPTION OF THE INVENTION

While the present invention is applicable to intraocular lenses and lenses used in spectacles, it will be described in connection with contact lenses. The present invention relates to lenses having a UV absorbing agent bonded to its polymeric lens material. The absorbing agent is water soluble and has a molecular structure which contains one or two UV absorbing components thereon which may either be the same or different from each other. The agent is bound to the polymeric lens material exoskelatally.

The present invention employs a reactive ultraviolet absorbing agent of the following formula:

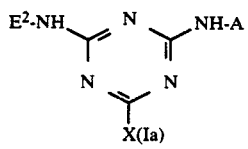

where
X=Cl or F;
A=an ultraviolet radiation absorbing component; and
$E^2$=an aqueous soluble moiety or an ultraviolet radiation absorbing component.

The ultraviolet absorbing components may be the same or different and are selected from suitable radicals of essentially any UV absorbing compounds; however, if both A and $E^2$ are UV absorbing compounds, at least one of them should bring the structure of formula I water solubility.

Typical radicals of UV absorbers are those radicals of UV absorbers disclosed in the following patents, all of which are incorporated herein by reference. U.S. Pat. Nos. 3,041,330, 3,159,646, 3,213,058, 3,214,436, 4,418,000, 4,418,001, 4,418,002, 4,826,978, 3,493,539, 3,399,173, 4,880,859, U.S. Pat. No. 4,785,063, Ser. No. 218,188, German 1,495,870, British 981,539, European 133,164.

UV absorbers of interest to the invention includes: benzoic acid esters, cyano and carbomethoxy acrylates, oxalic acid diamides, and hydroxyphenyltriazines.

Particularly suitable for use in the instant invention as UV absorber groups are the radicals of the benzophenones and benzotriazoles. Also of particular interest are the radicals of p-(benzoic and salicylic) acids. More specifically, the UV-absorbers of interest include, without limitation, Oxalic acid diamides, for example 4,4'-dioctyloxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy-disubstituted oxanilides and mixtures of o- and p-ethoxy-disubstituted oxanilides.

2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine.

2-(2'-Hydroxyphenyl)benzotriazoles, for example the 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-sec-butyl-5'-tert-butyl, 4'-octoxy, 3',5'-di-tert-amyl and 3',5'-bis(α,α-dimethylbenzyl) derivatives.

2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.

Esters of substituted and unsubstituted benzoic acids, for example, 4-tert-butylphenyl salicylate, phenyl salicylate, octylphenyl salicylate, dibenzoylresorcinol, bis(4-tert-butylbenzoyl)-resorcinol, benzoylresorcinol, 2,4-di-tert-butylphenyl 3,5-di-tert-butyl-4-hydroxybenzoate and hexadecyl 3,5-di-tert-butyl-4-hydroxybenzoate.

Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxycinnamate, methyl α-carbomethoxy-p-methoxycinnamate and N-(β-carbomethoxy-β-cyanovinyl)-2-methylindoline.

The ultraviolet radiation absorbing components A and E are preferably selected from the group including:

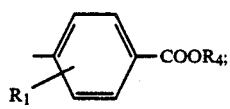

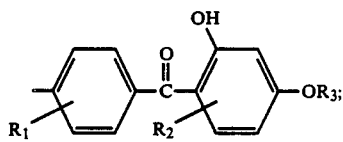

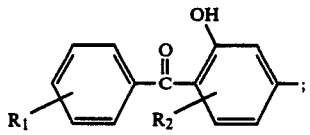

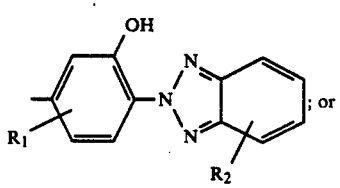

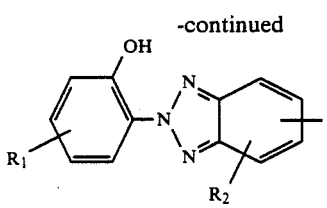

where $R_1$-$R_2$ are selected from the group consisting of H, alkyl chains varying from $C_1$ to $C_{18}$ preferably $C_1$ to $C_7$, more preferably $C_1$-$C_4$, and the corresponding alkoxy groups thereto, halogen, nitro, hydroxy, carboxy, sulfo, and salts such as alkali metal salts, for example sodium sulfonate; and $R_3$ and $R_4$ are each selected from H and $C_1$-$C_{18}$ alkyl, salts, for example sodium sulfonate; and $R_3$ and $R_4$ are each selected from H and $C_1$-$C_{18}$ alkyl, preferably $C_1$-$C_7$ alkyl, more preferably $C_1$-$C_4$ alkyl.

It is also preferred that the aqueous soluble moiety have the formula:

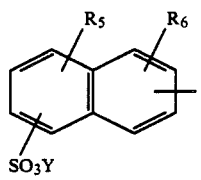

where Y is an amine salt or an alkali salt; and $R_5$ and $R_6$ are selected from the group consisting of hydrogen, alkyl chains varying from $C_1$ to $C_{18}$, preferably $C_1$-$C_7$ alkyl, more preferably $C_1$-$C_4$alkyl, and the corresponding alkoxy groups, halogen, nitro, hydroxy, carboxy, sulfonic acid, or salts such as the sodium salt.

Other solubilizing groups will be apparent to those of ordinary skill from the dyestuff art.

The compounds of formula I can be prepared by reacting compounds A-NH$_2$ and E$^2$NH$_2$ with cyanuric acid trihalide. Basically, mono amine substituted UV absorber is reacted with a trihalo triazine. The product is then reacted with either another amino-substituted UV absorber or a solubilizing moiety. Alternatively, an amino-substituted solubilizing moiety can be reacted with the trihalo triazine first and then an amino-substituted UV absorber is reacted with the product. The process will be more specifically seen with reference to the benzophenones in the Examples.

The compounds of the polymeric lens material may vary so long as there is present in the monomer mixture a component which will provide the polymer with the required exoskeletal functional groups. The required exoskeletal functional groups include any group that is coreactive with a halogen substituted triazine such that a covalent bond is formed between the lens material and the triazine molecule, usually with the elimination of hydrogen halide. Such groups, prior to reacting include, but are not limited to: hydroxy, amino, amido, mercapto, carboxy, etc.

Monomers having the above groups which are suitable for use in the invention include without limitation: hydroxyalkyl esters of polymerizable unsaturated acids, such as acrylic, methacrylic, fumaric, maleic, etc; unsaturated acids per se, such as acrylic, methacrylic, fumaric, maleic, etc; heterocyclic N-vinyl lactams, such as N-vinyl pyrrolidone, etc; noncyclic amides such as N-(1,1-dimethyl-3-oxobutyl)-acrylamide; amino alkyl esters of unsaturated acids such as 2-aminoethylacrylate, methacrylate, fumarate, or maleate; mercapto alkyl esters of unsaturated acids such as 2-mercapto ethyl acrylate, methacrylate, fumarate or maleate.

Other suitable monomers and reactive groups suitable for reacting with the halotriazine will be apparent for those of ordinary skill.

In addition to the monomers having the required halotriazine coreactive groups, the lens material may have a number of other monomeric components which do not have the stated reactive groups or such groups serve other purposes as when such a monomer is utilized as a crosslinking agents. The monomer, once crosslinking has taken place, is generally not available for interaction with the halotriazine. However, if more than two suitable reactive groups are present, such a monomer may indeed provide suitable reactive sites for covalently bonding to the halotriazine. Typical crosslinking agents include, without limitations:
ethyleneglycol dimethacrylate,
diethyleneglycol bis allyl carbonate,
etc.

A highly suitable and preferable lens material is hydroxyethylmethacrylate (HEMA) as disclosed in U.S. Pat. No. 2,976,576 and U.S. Pat. No. Re. 27,401. Two acceptable "hard" lens materials are cellulose acetate butyrate and polymethylmethacrylate (PMMA).

The UV-absorber compounds of the invention may be used to make contact lenses absorb UV radiation by bonding them to the lens polymer material in the same way as the halo triazine dyes are used to tint contact lenses. For example, a practitioner may place a preformed contact lens in a UV absorber solution. In a standard procedure, a contact lens is rinsed with deionized water and placed in a dry vial. Base solution (typically 10% Na$_3$PO$_4$.12H$_2$O (aq) solution) is added to the vial, followed by the UV absorber solution. The vial is shaken in a shaker bath, and the lens removed. The lens is rinsed with deionized water and extracted with 10% glycerine (aq) solution at 80° C. for two hours. The lens is once again rinsed with water, then stored in saline. This process is further improved if a quaternary ammonium salt is preferably provided in the UV absorber solution prior to placement of the lens material therein.

A number of ammonium quaternary salts may be used in practicing the improved process, including $$[A]_w[B]_z[C]_t[E]_vN^+Q^- \quad (I)$$

where
each of w, z, t and v is 0–4 and w+z+t+v=4.
Q is a counterion selected for HSO$_4^-$, F$^-$, Cl$^-$, Br$^-$, I$^-$, CH$_3$COO$^-$, OH$^-$, BF$_4^-$,

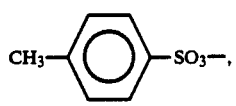

PF$_6^-$, and H$_2$PO$_4^-$.

A, B, C, and E are each selected from $C_{1-18}$ alkyl preferably $C_{1-7}$alkyl, more preferably $C_{1-4}$alkyl, phenyl or phenyl-$C_{1-4}$alkyl, in which the phenyl ring is unsubstituted or substituted by $C_1$-$C_8$alkyl, $C_1$-$C_8$alkoxy, halo, hydroxy, phenoxy, nitro, carboxy, acetamido, phenyl, or benzyl, cycloalkyl having 5–6 ring members, for example, tri-$C_{1-4}$alkylbenzylammonium$_2$ chloride, triethylbenzylammonium chloride, tetraC$_{1-4}$alkylammonium hydrogen sulfate, especially tetrabutylammonium hydrogen sulfate, phenyltriC$_{1-4}$alkylammonium chloride, especially phenyl trimethylammonium chloride, benzyltriC$_{1-4}$alkylammonium chloride, especially benzyltributylammonium chloride, tetraC$_{1-4}$alkylammonium bromide, especially tetra butyl ammonium chloride or bromide, and tetraethylammonium chloride or bromide.

The following examples illustrate, but do not limit the instant invention.

EXAMPLE I

Cyanuric chloride, 18.4 g, was dissolved in 150 ml of warm acetone and the solution was poured into a stirred mixture of 200 g of ice and 200 ml of water. To this cyanuric chloride suspension was added simultaneously an aqueous solution made by dissolving 15.3 g of 4-amino salicyclic acid in 120 ml of water containing 5.4 g of sodium carbonate and a dilute sodium carbonate solution (5.4 g in 50 ml of H$_2$O). After addition, the mixture was stirred at 5°–10° C. for one and a half hour. The final pH of the mixture was 6.0. The solid was collected by filtration, washed with water and air dried to obtain 30.6 g of 2,4-dichloro-6-[(3-hydroxy-4-carboxy)phenylamino]-s-triazine.

EXAMPLE II

To a mixture of 150 ml of acetone, 100 ml of water, 1 g of sodium carbonate and 6.5 g of dichloro-s-triazine, prepared as described in Example I above, was added an aqueous solution (100 ml) of 7-amino-1,3-naphthalene disulfonic acid, monopotassium salt (8.0 g) containing one gram of sodium carbonate. The resulting mixture was refluxed for two hours. Most of acetone was then distilled off until the pot temperature reached 80° C. The reaction mixture was cooled to about 10° C. The solid which formed was collected by filtration and dried to obtain 1.55 g of 2-chloro-4-[7-(1,3-disulfo)naphthylamino]-6-[(3-hydroxy-4-carboxy)phenylamino]-s-triazine and its sodium salts. More product (9.3 g) was obtained by adjusting the filtrate to pH=3.0 and collecting the precipitate.

EXAMPLE III

Proceeding in a manner similar to that described in Example II above, 9.0 g of 2,4-dichloro-6-[(3-hydroxy-4-carboxy)phenylamino]-s-triazine, 10.5 g of 3-amino-2,7-naphthalene disulfonic acid, monosodium salt, trihydrate and 3.0 g of sodium carbonate were interacted in water-acetone mixture to obtain 11.04 g of 2-chloro-4-[3-(2,7-disulfo)naphthylamino]-6-[(3-hydroxy-4-carboxy)phenylamino]-s-triazine and its sodium salts.

EXAMPLE IV

Following the procedure described in Example I above, 55.2 g of cyanuric chloride was interacted with 120 g of 7-amino-1,3-naphthalene disulfonic acid, monopotassium salt in water-acetone mixture to obtain 81.6 g of 2,4-dichloro-6-[7-(1,3-disulfo)naphthylamino]-s-triazine.

EXAMPLE V

Proceeding in a manner similar to that described in Example II above, 4.9 g of 2,4-dichloro-6-[7-(1,3-disulfo)naphthylamino]-s-triazine, 2.26 g of 2-(4-amino-2-hydroxyphenyl)benzotriazole and 2.1 g of sodium carbonate were interacted in water-acetone mixture to obtain 2-chloro-4-[(3-hydroxy-4-benzotriazo-2-yl)phenylamino]-6-[7-(1,3-disulfo)naphthylamino]-s-triazine and its sodium salts.

EXAMPLE VI

Proceeding in a manner similar to that described in Example II above, 47.4 g of 4-amino-2-hydroxy-4-methoxybenzophenone, 25.5 g of 2,4-dichloro-6-[7-(1,3-disulfo)naphthylamino]-s-triazine, and 10.5 g of sodium carbonate were interacted in water-acetone mixture to obtain 71.2 g of 2-chloro-4-[4-(2-hydroxy-4-methoxybenzoyl)phenylamino]-6-[7-(1,3-disulfo)naphthylamino]-s-triazine and its sodium salts.

The standard process for incorporating the reactive ultraviolet absorbing agent into the lens involves contacting the agent to the lens material, preferably under mild reaction conditions. In one method, for example, the lens is rinsed with deionized water and placed in a dry vial. Two milliliters each of a solution containing a reactive UV absorbing agent and diluted sodium carbonate solution are then added to the vial. The vial containing the solutions and the lens is placed in a vial rack in a shaker bath at a set temperature and speed. After a set predetermined period of time has elapsed, the lens is removed from the vial, rinsed with deionized water, and extracted with a 10% glycerine (aq) solution at 80° C. for two hours. The lens is then rinsed with water and stored in a 0.9% saline solution for 30 minutes. The transmission and/or absorbance spectrum of the lens can then be determined using a UV spectrophotometer.

It has also been found that the bonding of the ultraviolet absorbing agent and lens material may be enhanced by including an ammonium quaternary salt catalyst in the agent incorporating process. Examples of such ammonium quaternary salts include triethylbenzylammonium chloride, tetrabutylammonium hydrogen sulfate, phenyltrimethylammonium chloride, benzyltributylammonium chloride, tetrabutylammonium bromide, and tetramethylammonium chloride.

The following Example VII will illustrate the effect of different catalysts on the incorporation of reactive UV absorbing agents in contact lenses:

EXAMPLE VII

A series of corneal contact lenses was prepared and UV transmittance spectra were taken as set forth in the above-described standard process, except that 0.1 ml of an aqueous solution holding a catalyst was added to the vial containing the lens, a tri-sodium phosphate solution for maintaining a high pH and the aqueous solution having a UV blocking agent. The temperature of the bath was maintained at 45° C., the shaker bath speed was at 100 strokes per minute and the time the lenses remained in the shaker bath was two hours. A 1% aqueous solution of the compound of Example VI was employed as the reactive UV blocking agent solution.

Transmittance data from UV absorbing lenses prepared as above using various catalyst solutions were compared to transmittance data from lenses identically prepared except that no catalyst was employed. A sharp decrease in the transmittance curve for lenses prepared without a catalyst was found to occur around 360 nm, and transmittance spectra for these lenses exhibit a shoulder in the region from 275 to 360 nm with a small peak occurring around 290 nm. As is shown in Table I, the quaternary ammonium salt catalysts substantially improved the UV absorbing characteristics of the lenses.

TABLE I

| Catalyst | % T at 290 nm | Transmittance characteristics in the 275-360 nm range. |
|---|---|---|
| 1. no catalyst | 2.3% | shoulder |
| 2. 10% Tyloxapol (aq) | 6.9% | pronounced shoulder |
| 3. 10% Varsulf SBFA-30 (aq) | 4.6% | distinct shoulder |
| 4. 10% Pluronic F-127 (aq) | 2.3% | similar to no catalyst |
| 5. 5% triethylbenzylammonium chloride (aq) | <1% | no shoulder |
| 6. 5% cetylpyridinium chloride (aq) | 9.2% | very prominent shoulder |
| 7. 5% tetrabutylammonium hydrogen sulfate (aq) | <1% | no shoulder |
| 8. 5% p-dimethylaminopyridine | 2.3% | similar to no catalyst |

The following Example VIII further illustrates the effectiveness of different quaternary ammonium salts on the incorporation of absorbing agents in contact lenses:

EXAMPLE VIII

A series of corneal contact lenses was prepared and UV transmittance and absorbance spectra were taken as set forth in Example VII, except that 0.2 ml of a 5% aqueous solution of a quaternary ammonium salt was added to the vial containing the lens, the tri-sodium phosphate solution, and the solution containing a UV blocking agent. The temperature of the bath was maintained at 45° C., the shaker bath speed was 110 strokes per minute, and the time the lenses remained in the shaker bath was two hours. A 1% aqueous solution of the compound of Example VI was employed as the reactive UV blocking agent solution. Five percent (5%) aqueous solutions of (1) tetrabutylammonium hydrogen sulfate, (2) phenyltrimethyammonium chloride, (3) benzyltributylammonium chloride, (4) tetrabutylammonium bromide, (5) tetramethylammonium chloride and (6) a polyquat solution were tested in this example.

Transmittance data from UV absorbing lenses prepared utilizing (1), (2), (3), and (4) showed the superior UV absorbing characteristics of these lenses compared to lenses prepared without any catalyst. The transmittance peak at around 290 nm that appeared in a lens prepared without any catalyst and the shoulder in the 275 to 360 nm region was not present in lenses prepared in the presence of (1), (2), (3) or (4). Absorbance of UV radiation in the 290 nm to 400 nm region was greatest for lenses prepared using (3) followed by those prepared using (4), (1) and (2) respectively. The use of (5) as a catalyst produced lenses with UV absorbing characteristics only slightly better than lenses prepared in the absence of a catalyst. However, the use of (6) as a catalyst retarded the incorporation of the UV absorbing agent in the lens, and lenses prepared in the presence of (6) showed poor UV absorption in the 260 to 400 nm region.

EXAMPLE IX

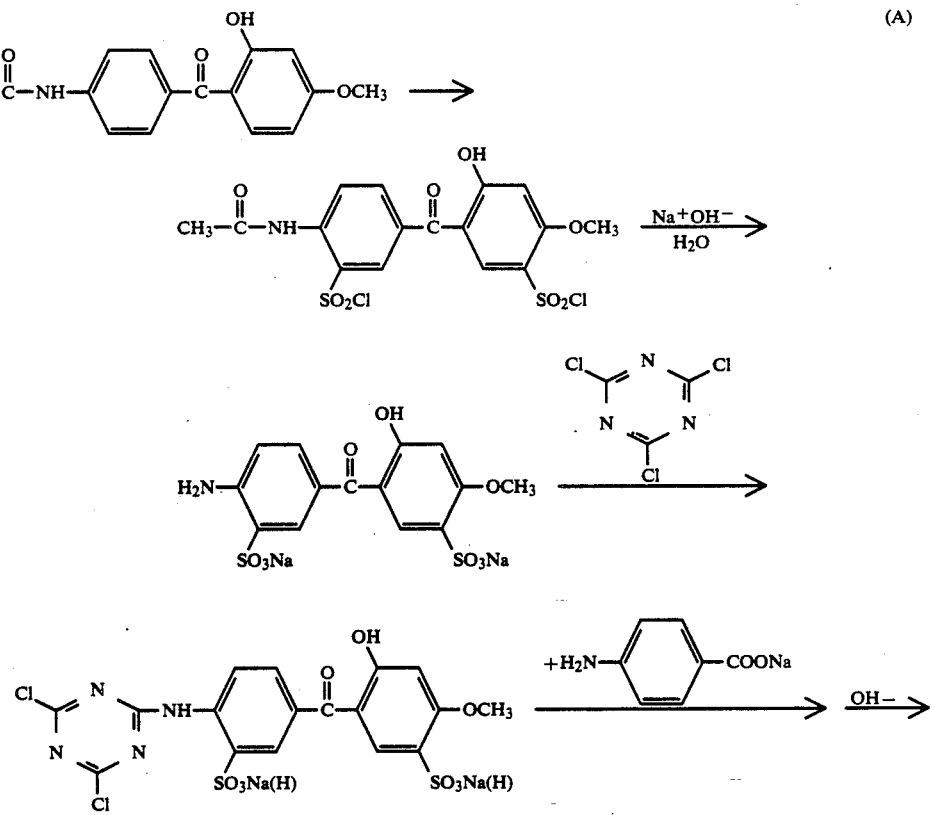

(A)

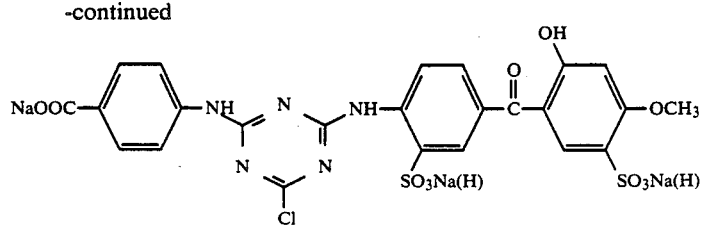

A. 100 ml of chlorosulfonic acid was charged into a 500 ml flask and cooled to 5° C. Then, 20 g of 4'-acetamido-2-hydroxy-4-methoxybenzophenone was added to the flask over a period of 15 minutes. The reaction was maintained at a temperature below 20° C. during the addition. After the addition, the reaction mixture was stirred at room temperature for 16 hours. The reaction mixture was added dropwise into 1.5 liters of ice water and a precipitate was formed. The precipitate was collected and washed two times with 50 ml of ice water, then air dried.

The precipitate was placed in 120 ml of water, and dilute NaOH was slowly added until the solid dissolved. The solution had a pH of 12 and was kept at 90° C. for 30 minutes, then cooled to room temperature.

B. A cyanuric chloride suspension was prepared by dissolving 12 g of cyanuric chloride in 50 ml of warm acetone and quickly dispersed into 150 ml of ice water. At 5° C., the solution from part A was quickly added to the cyanuric chloride suspension. The reaction mixture was stirred at approximately 10° C. for three hours whereby a gel material was formed. Water was added to dilute the gel material until the total volume was 400 ml and the pH was 3.0.

C. A mixture of 100 ml of the gel material solution from part B, 2.5 g of p-aminobenzoic acid which was predissolved in dilute base, 3.0 g of sodium carbonate and 100 ml of water was heated at 90° C. for three hours. The mixture was then cooled to room temperature and the pH was adjusted from 9.2 to 7.0 with 3N.HCl. The solution was then evaporated to dryness and the residue was extracted with hot acetone several times to obtain 2-chloro-4-[(4-carboxy)phenylamino]-6-(2-sulfo-4-[(hydroxy-4-methoxy-5-sulfo)benzoyl]-phenylamino)-s-triazine (compound A) and/or its sodium salts as a yellow solid, which was the ultraviolet radiation absorbing agent.

EXAMPLE X

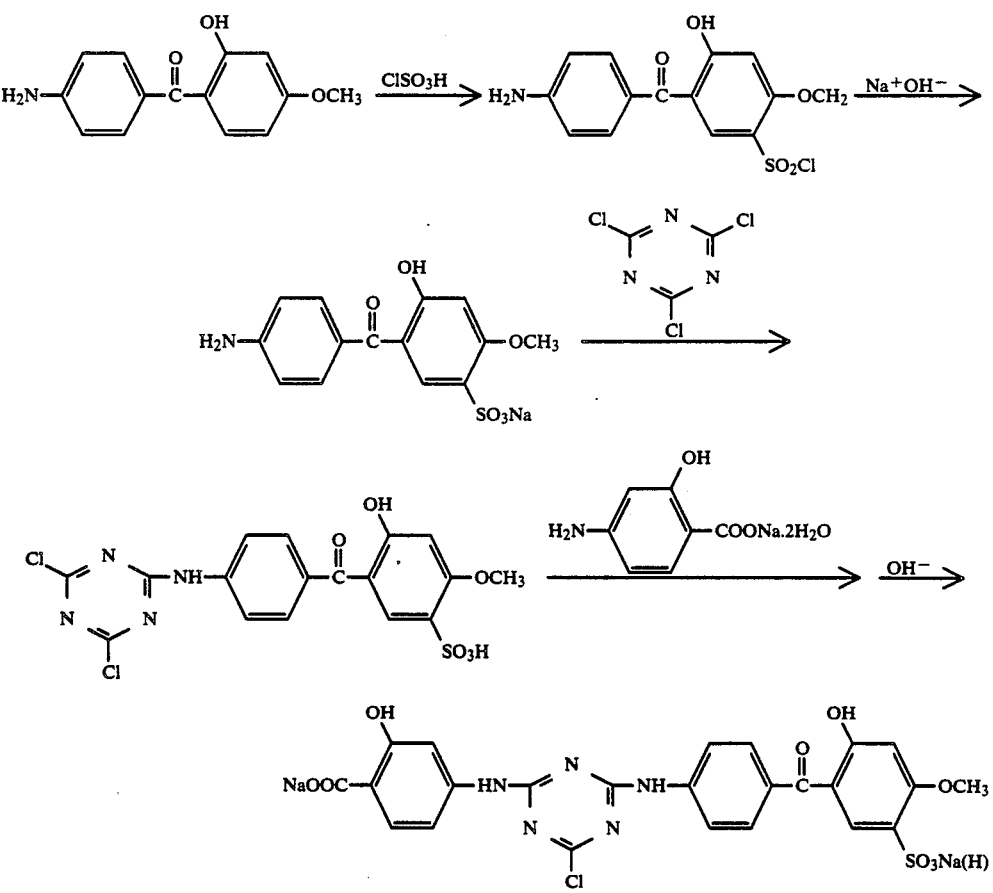

(B)

A. 100 ml of chlorosulfonic acid was charged into a flask and cooled at approximately 5° C. in an ice bath. 20 g of 4'-amino-2-hydroxy-4-methoxybenzophenone was slowly added over a period of 20 minutes. The addition was performed at a temperature below 20° C. After addition, the reaction mixture was stirred at room temperature for four hours. The mixture was then quenched dropwise into 1.5 liters of ice water and a precipitate was formed. The precipitate was collected, washed two times with 50 ml of ice water, and air dried to obtain 28.5 g.

28.3 g of the precipitate was suspended in 150 ml of water. 25% NaOH was slowly added to dissolve the precipitate and the pH of the solution was adjusted to 11.5 and was kept at 90° C. for thirty minutes, then cooled to room temperature. The resulting orange solution had a total volume of 300 ml.

B. A cyanuric chloride dispersion was prepared by dissolving 15 g of cyanuric chloride in 70 ml of warm acetone and quickly dispersed into 200 ml of ice water. The beaker which had been holding the cyanuric chloride was rinsed with an additional 30 ml of acetone, which was then added to the dispersion. The dispersion was cooled to 5° C.

The orange solution from part (A) was quickly added into the cyanuric chloride dispersion and the resulting mixture was stirred at between approximately 5° to 10° C. for three hours. The pH of the mixture was 2.7. A small amount of water was added, and the final volume was adjusted to 900 ml.

C. 225 ml of the mixture from (B), 4.2 g of 4-aminosalicylic acid, sodium salt dihydrate, 3.0 g of $Na_2CO_3$ and 150 ml of water was mixed. The pH was adjusted to 9.5 by adding NaOH, and the reaction mixture was heated at 90° C. for three hours, then cooled to room temperature. The pH was then adjusted to 7.0 with 3N.HCl. The mixture was evaporated to dryness. The residue was extracted with hot acetone several times to get 17.79 g of 2-chloro-4-[(3-hydroxy-4-carboxy)phenylamino]-6-{4-[(2-hydroxy-4-methoxy-5-sulfo)-benzoyl]phenylamino)-s-triazine (Compound B) and its sodium salts, as a yellow solid, which was the UV absorbing agent.

EXAMPLE XI

Proceeding in a manner similar to that described in Example IX, part C above, except that 4-amino salicyclic acid was substituted for p-aminobenzoic acid, resulted in the formation of 2-chloro-4-[(3-hydroxy-4-carboxy)phenylamino]-6-{2-sulfo-4-[(2-hydroxy-4-methoxy-5-sulfo)benzoyl]phenylamino}-s-triazine and its sodium salts.

EXAMPLE XII

Proceeding in a manner similar to that described in Example X, part C above, except that p-aminobenzoic acid was substituted for 4-aminosalicyclic acid to obtain 2-chloro-4-[(4-carboxy)phenylamino]-6-{4-[(2-hydroxy-4-methoxy-5-sulfo)benzoyl]phenylamino}-s-triazine and its sodium salts.

A typical process for applying the absorbing agent to the lens is now set forth. A mixture of 2 ml of 0.05 to 5.0% (aq) stock solution of ultraviolet radiation absorbing agent, 2 ml of 5 to 10% (aq) $Na_3PO_4.12H_2O$, and 0.2 ml of 1 to 10% (aq) solution of tetrabutylammonium bromide was prepared and heated at 50° C. for 60 minutes with agitation. A clear lens comprised of hydroxyethyl methacrylate (HEMA) was then soaked in the mixture until the agent bonded to the lens. The lens was then neutralized with a buffered saline solution (pH=7.0), after which the lens was extracted with 10% glycerine in an extraction bath until there was no UV absorbing agent leaching out. This was determined by a UV spectrophotometer. After the extraction process, the lens was boiled in distilled water, and then buffered with saline to remove any remaining glycerine.

It has been found that adding two different UV absorbing components onto the agent can provide a contact lens which will absorb a wide range of wavelengths. For example, the absorbing component Tinuvin ® P (available from Ciba Giegy Corporation), which is a benzotriazole type absorber, blocks UV radiation from about 280 nm to 360 nm very well, but it does not block well at about 250 nm to 275 nm. The 4-aminobenzoic acid type component blocks radiation from 190 nm to 316 nm very well, but little higher. By combining the two components onto a single molecule according to the present invention, the resultant UV absorbing agent, and hence a lens incorporating the agent, will have excellent UV absorption from about 190 nm to 360 nm (the union of the spectra of the two components).

Similarly, when a benzophenone type component (which also blocks UV radiation from about 280 nm to 360 nm) is added to 4-aminobenzoic acid type component in place of the Tinuvin ® P above, the resulting reactive UV absorbing agent will have excellent UV absorption from about 190 nm to 360 nm.

It is also possible to add similar or identical UV absorbing components onto the agent. In such a case, the amount of agent needed to provide an effective radiation absorbing lens will be decreased. The decrease of agent on the lens greatly reduces the structural weaknesses associated with lenses having single-component absorbing agents.

What is claimed is:

1. An ultraviolet radiation absorbing agent for bonding to an ocular lens, wherein said agent has the formula:

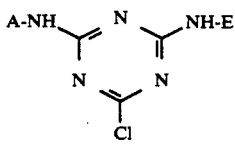

I wherein A and E are ultraviolet radiation absorbing components which are either identical to or dissimilar to each other, or of the formula

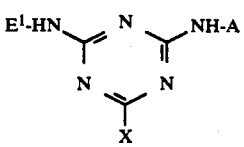

II where
X=Cl or F;
A=an ultraviolet radiation absorbing component selected from the group consisting of p-benzoic acid, p-salicyclic acid, substituted benzophenone, substitued benzotriazoles, benzoic acid esters, acrylates, oxalic acid diamides, and hydroxy phenyltriazines;

E=an ultraviolet radiation absorbing component selected from the group consisting of p-aminobenzoic acid, p-aminosalicylic acid, substituted benzophenone and substituted benzotriazoles, benzoic acid esters, acrylates, oxalic acid diamides, and hydroxy phenyltriazines;

$E^1$=an aqueous soluble moiety of the formula

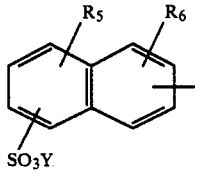

where

Y is an amine salt or an alkali metal salt; and $R_5$–$R_6$ are selected from the group consisting of hydrogen, alkyl chains varying from $C_1$ to $C_{18}$, $C_1$–$C_{18}$alkoxy, halogen, nitro, hydroxy, carboxy, sulfonic acid or a salt thereof.

2. The compounds in claim 1 wherein at least one of A and E is selected from the group consisting of

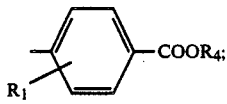

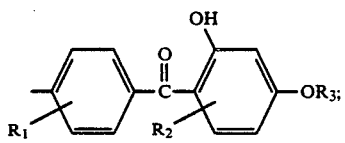

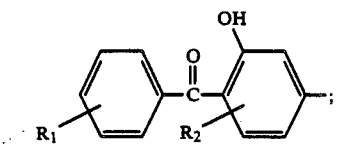

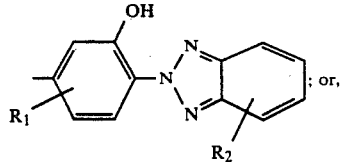

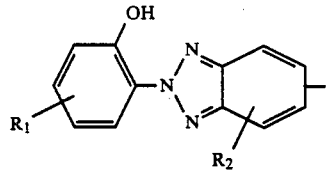

where
$R_1$–$R_2$ are independently selected from the group consisting of hydrogen, alkyl chains varying from $C_1$ to $C_{18}$, $C_1$–$C_{18}$alkoxy, halogen, nitro, hydroxy, carboxy, sulfonic acid, or sulfonic acid alkali metal salts and $R_3$ and $R_4$ are independently selected from hydrogen and $C_1$–$C_{18}$alkyl.

3. The compound of claim 2 wherein said $R_1$, $R_2$, $R_3$ and $R_4$ $C_1$–$C_{18}$alkyl is $C_1$–$C_4$alkyl, and said $R_1$ and $R_2$ $C_1$–$C_{18}$alkoxy is $C_1$–$C_4$alkoxy.

4. The ultraviolet radiation absorbing agent of claim 1, wherein said agent is selected from the group consisting of 2-chloro-4-[(4-carboxy)phenylamino]-6-{2-sulfo-4-[(2-hydroxy-4-methoxy-5-sulfo)benzoyl]-phenylamino}-s-triazine; 2-chloro-4-[(3-hydroxy-4-carboxy)phenylamino]-6-{4-[(2-hydroxy-4-methoxy-5-sulfo)benzoyl]phenylamino}-s-triazine; 2-chloro-4-[(3-hydroxy-4-carboxy)phenylamino]-6-{2-sulfo-4-[(2-hydroxy-4-methoxy-5-sulfo)benzoly]phenylamino}-s-triazine; 2-chloro-4-[(4-carboxy)phenylamino]-6-{4-[(2-hydroxy-4-methoxy-5-sulfo)benzoyl]phenylamino}-s-triazine; and sodium salts thereof.

5. The compound of claim 1 wherein said $R_5$ and $R_6$ $C_1$–$C_{18}$alkyl and $C_1$–$C_{18}$alkoxy are selected from $C_1$–$C_4$alkyl and $C_1$–$C_4$alkoxy.

6. The compound in claim 1, wherein said compound is selected from the group consisting of; 2-chloro-4-[7-(1,3-disulfo)naphthylamino]-6-[(3-hydroxy-4-carboxy)-phenylamino]-s-triazine; 2-chloro-4-[3-(2,7-disulfo)-naphthylamino]-6-[(3-hydroxy-4-carboxy)-phenylamino]-s-triazine; 2-chloro-4-[(3-hydroxy-4-benzotriazo-2-yl)phenylamino]-6-[7-(1,3-disulfo)naphthylamino]-s-triazine; 2-chloro-4-[4-(2-hydroxy-4-methoxybenzoyl)phenylamino]-6-[7-(1,3-disulfo)naphthylamino]-s-triazine.

7. The compound of claim 1 wherein A and E are different components.

8. The compound of claim 1 wherein A and E are identical components.

* * * * *